United States Patent [19]

Dreibelbis et al.

[11] Patent Number: 5,391,343

[45] Date of Patent: Feb. 21, 1995

[54] THIN-WALLED ARTICLES OF POLYURETHANEUREA

[75] Inventors: Richard L. Dreibelbis, Waynesboro; Nathan E. Houser, Afton, both of Va.; Jacob Lahijani, Wilmington, Del.

[73] Assignee: E. I. du Pont de Nemours and Company, Wilmington, Del.

[21] Appl. No.: 965,600

[22] Filed: Oct. 26, 1992

[51] Int. Cl.$^6$ .......................... B29D 7/00; B28B 1/38; C08J 3/20; C08L 75/00
[52] U.S. Cl. ........................... 264/216; 264/212; 264/214; 264/215; 264/305; 264/308; 524/589; 524/590; 528/44; 528/61; 528/64
[58] Field of Search ............... 264/212, 214, 215, 216, 264/305, 308; 528/44, 61, 64; 524/589, 590

[56] References Cited

U.S. PATENT DOCUMENTS

| | | | |
|---|---|---|---|
| 2,814,834 | 12/1957 | Hess et al. | 18/58.6 |
| 3,553,308 | 1/1971 | Kobayashi et al. | 264/305 |
| 5,000,899 | 3/1991 | Dreibelis et al. | 528/64 |
| 5,132,129 | 7/1992 | Potter et al. | 427/2 |

FOREIGN PATENT DOCUMENTS

| | | | |
|---|---|---|---|
| 6633847 | 8/1985 | Japan | C08J 3/08 |
| 2181691 | 4/1987 | United Kingdom . | |

*Primary Examiner*—Paul R. Michl
*Assistant Examiner*—P. Niland

[57] ABSTRACT

Certain polyether-based or polyester-based polyurethaneureas in solutions of organic solvent at a 12 to 20% concentration are particularly suited for use in a mandrel-dipping process for producing thin-walled elastic articles, such as surgical gloves, which are more resistant to puncture and tear than conventional surgical gloves made from rubber latex.

2 Claims, No Drawings

THIN-WALLED ARTICLES OF POLYURETHANEUREA

BACKGROUND OF THE INVENTION

FIELD OF THE INVENTION

This invention relates to polyurethaneurea solutions and thin-walled elastic articles prepared therefrom. More particularly, the invention concerns certain polyurethaneurea solutions that can be made into thin-walled articles, such as surgical gloves, condoms and the like, which have superior resistances to puncture and tear, as compared to similar articles made from conventional rubber latexes.

DESCRIPTION OF THE PRIOR ART

Elastomeric gloves, such as those made from conventional rubber latex, are known for use in sterile, surgical, and chemical environments. Such gloves should have ease of donning, good fit, comfort, and tactility (i.e., the ability to feel objects through the gloves), low set and high resistance to tear and puncture. Conventional rubber-latex gloves are made by dipping a mandrel which is pre-coated with a coagulant into an aqueous rubber emulsion. To provide gloves with adequate strength and avoid pinholes, the dipped rubber-latex gloves typically are in the range of 0.18 to 0.20 mm thick. Such thicknesses somewhat limit the glove user's digital dexterity and tactility.

Hess et al, U.S. Pat. No. 2,814,834, and Kobayashi et al, U.S. Pat. No. 3,553,308, disclose substituting a synthetic polyesterurethaneurea for rubber latex to produce gloves or other thin-walled articles, by "reaction dipping" methods which include (a) coating a mandrel by dipping it into a solution of an isocyanate-terminated polyester prepolymer, (b) then dipping the thusly-coated mandrel into a solution of a diamine chain-extending agent to react the diamine with the isocyanate-terminated prepolymer to form a polyesterurethaneurea coating on the mandrel, (c) removing the solvent from the coating and (d) then stripping the coating from the mandrel to provide the finished article. Potter et al, U.S. Pat. No. 5,132,129 discloses another such process wherein an amine-terminated prepolymer is dip-coated onto a mandrel and then treated further by dipping into or being sprayed with a solution of poly-functional curing agent which reacts with the amino ends groups to extend and/or crosslink the prepolymer chains. To improve certain mechanical properties, glove thickness can be increased by repeating the double-dipping sequence several times. Although useful, reaction dipping requires two solutions, multiple dips and a long curing step. Also, the prepolymer and diamine solutions are susceptible to degradation by water and oxygen, respectively.

Polyurethaneurea solutions also have been suggested for coating fabric gloves. For example, Ishiwata, Japanese Patent Application Publication 60-033847 (1985), discloses dissolving spandex fibers, prepared from polyether glycol, 4,4'-diphenylmethane diisocyanate, and ethylene diamine, in dimethylformamide containing 0.05 to 10% lithium chloride to form a solution having 19% solids and a solution viscosity of 50 poise. Then, fabric gloves, fitted on a metal mandrel are dipped into and removed from the solution and the dimethylformamide solvent is allowed to evaporate, thereby completing the coated glove. Ishiwata notes that when lithium chloride is omitted from the solution, gel formation and attendant glove fabrication difficulties are encountered.

A purpose of the present invention is to prepare thin-walled elastic articles, particularly surgical gloves of improved properties, from polyurethaneurea solutions by a process that does not include metal chlorides, a chemical curing step or a spandex-fiber dissolving step and does not suffer from the shortcomings of the above-described art.

SUMMARY OF THE INVENTION

The present invention provides an improved solution of a polyurethaneurea in an organic solvent, the polyurethaneurea being a polyesterurethaneurea or a polyetherurethaneurea. The solution is substantially free of metal chlorides (i.e., containing no more than 0.05%, based on the weight of polyurethaneurea) and is particularly suited for use in producing thin-walled elastic articles, such as surgical gloves, condoms and the like. In accordance with the improvement of the invention, the solution has a polyurethaneurea concentration in the range of 12% to 20%, preferably 14 to 17%, by total solution weight, and a viscosity in the range of 25 to 125 poise, preferably 50 to 100 poise. The polyurethaneurea is formed by reacting an organic diisocyanate, preferably methylene-bis-(4-phenylisocyanate), with a polymeric diol of 3,000 to 6,000 number average molecular weight to form an isocyanate-capped prepolymer having an isocyanate (NCO) end-group concentration in the range of 1.4 to 2.0% and then chain extending the prepolymer with a diamine. N,N-dimethylacetamide is a preferred solvent for the polyurethaneurea solutions. When the polyurethaneurea is a polyesterurethaneurea, the polymeric diol is a polyester diol derived from the reaction of adipic acid with a mixture of ethylene glycol (2G) and 1,4-butanediol (4G), in the weight ratio of 2G/4G in the range of 20:80 to 80:20, preferably 40:60 to 75:25, and the chain-extending diamine, preferably is 1,3-diaminocyclohexane or ethylene diamine. When the polyurethaneurea is a polyetherurethaneurea, the polymeric diol is a polyether diol derived from a mixture of tetrahydrofuran (THF) and 3-methyltetrahydrofuran (3MeTHF), in a weight ratio of THF/3MeTHF in the range of 96/4 to 80/20, and the chain-extending diamine preferably is ethylene diamine.

Thin-walled elastic articles are prepared from the above-described solutions of the invention by degassing the solution, dip-coating a mandrel with the degassed solution, evaporating the solvent from the coating and finally removing the thusly formed article from the mandrel. A preferred article of the process is a surgical glove. Surgical gloves prepared from solutions according to the invention can have about half the thickness of conventional rubber latex surgical gloves and still possess superior tear and puncture resistance, as well as desirable set, tactility and comfort characteristics.

DETAILED DESCRIPTION OF PREFERRED EMBODIMENTS

The invention will now be described in greater detail with particular reference to the fabrication of thin-walled surgical gloves from polyurethaneurea solutions of the invention.

The term "thin-walled", as used herein, generally refers to a thickness of no greater than about 0.18 millimeters. The term polyurethaneurea refers to a long chain synthetic polymer that consists essentially of alternating "soft segments" of polyether or polyester and "hard segments" derived from the reaction of an isocyanate and a diamine chain extender. The isocyanate end-group content of isocyanate-terminated prepolymer is described by the % NCO. "Molecular weight" refers to number average molecular weight. Also, several abbreviations are used herein, with the following meanings:

2G ethylene glycol
4G 1,4-butanediol
6 adipic acid
THF tetrahydrofuran
3MeTHF 3-methyltetrahydrofuran
MDI methylene bis-(4-phenylisocyanate)
PICM methylene bis-(4-cyclohexylisocyanate)
EDA ethylenediamine
HMPD 1,3-diaminocyclohexane
1,2PDA 1,2-diaminopropane
1,3PDA 1,3-diaminopropane
MXD metaxylylene diamine
DMAc N,N-dimethylacetamide In accordance with the present invention, polyurethaneurea solutions are prepared by dissolving polyurethaneurea in a polar aprotic solvent, such as dimethylacetamide (DMAc), dimethyl sulfoxide, N-methylpyrrolidone, dimethylformamide or the like. The solution has a falling-ball viscosity in the range of 25 and 125 poise and has a polyurethaneurea concentration in the range of 12 to 20%. Solutions with viscosities greater than about 125 poise tend to trap air bubbles and are difficult to evenly dip-coat onto a mandrel. Solutions with viscosities lower than about 25 poise often wet the mandrel unevenly. Solutions with a polymer concentration in the range of 14 to 17% and a viscosity in the range of 50 to 100 poise are preferred. The lower ends of the preferred ranges are particularly preferred when two separate dipping and drying steps are employed to form articles with greater thickness.

When the polyurethaneurea for use in the invention is polyester-based, the polyurethaneurea is preferably formed from a hydroxyl-terminated adipate copolyester (2G/4G-6), which is the reaction product of adipic acid (6) and a mixture of ethylene glycol (2G) and 1,4-butanediol (4G). Typically, the weight ratio of 2G to 4G is in the range of 20:80 to 80:20, and preferably in the range 40:60 to 75:25. The hydroxyl-terminated adipate copolyester is reacted with excess diisocyanate to produce isocyanate-terminated prepolymer. Typically, the isocyanate end-group content (i.e., "% NCO") of the prepolymer is greater than 1.4% to avoid excessive tackiness and less than 2.0% to avoid excessive load power in the final article. The isocyanate-terminated prepolymer which is then chain extended with a diamine to form the polyesterurethaneurea. To control molecular weight, a minor amount of a secondary amine, such as diethylamine can be used as a chain terminator. Suitable diisocyanates include MDI, PICM and the like. MDI is preferred. Suitable diamines include EDA, 1,2-PDA, 1,3-PDA, HMPD, MXD, mixtures thereof and the like. HMPD is preferred. Suitable solvents for solutions of the invention include dimethylformamide, DMAc, dimethyl sulfoxide, and N-methylpyrrolidone. DMAc is preferred. Typically, the copolyester glycol has a molecular weight in the range of 3,000 to 6,000. Polyesterurethaneureas made from copolyesterdiol 2G/4G-6 by capping with MDI and chain extending with HMPD are preferred for the best balance of properties for glove fabrication.

Polyetherurethaneureas suitable for the solutions of the present invention have polyether segments formed by copolymerization of THF with 3MeTHF in a ratio of about 96/4 to 80/20. The diol-terminated polyether obtained from these ingredients is reacted with a diisocyanate to form an isocyanate-terminated polyether which is chain extended with a diamine (or a mixture of diamines) and then usually chain terminated with a secondary amine, such as diethylamine. Polyetherurethaneureas suitable for use in the invention are preferably formed with MDI as the diisocyanate and EDA as the diamine chain extender.

Various known additives can be included in the polyurethaneurea solutions of the invention and thin-walled articles made therefrom for various purposes. For example, phenolic antioxidants, such as Cyanox* 1790 (sold by American Cyanamid Co.), Santowhite Powder* 345 (sold by Monsanto Chemical Co.), the condensation polymer from p-cresol and divinyl benzene, copolymers containing tertiary amine such as DIPAM/DM (diisopropylaminoethylmethacrylate and n-decylmethacrylate in a 70/30 weight ratio), or the polyurethane formed by reaction of t-butyldiethanolamine and methylene-bis-(4-cyclohexylisocyanate) and the like. Among other additives suitable for use in the solutions and products of the invention are conventional agents such as thermal stabilizers, UV stabilizers, pigments, dyes, titanium dioxide, and the like.

To prepare thin-walled shaped articles, such as gloves, from the solutions of the invention, entrapped and/or dissolved air or other gases are first removed from the solution. Gas removal can be accomplished by applying vacuum on the solution for a few minutes. Then, a mandrel of the desired size and shape is dipped into the degassed solution, preferably at an angle of about 80 to almost 90 degrees to the vertical with the mandrel "fingers" entering first and the palm facing upward. The mandrel is kept immersed in the solution for about 5 to 30 seconds. The solution temperature is typically at about 20 to 30° C. The mandrel may be hot or at room temperature depending on desired glove thickness. Hot mandrels result in thinner gloves.

After immersion, the mandrel is slowly removed (over a period of about 10 to 15 seconds) from the solution and excess solution allowed to drain for about 1 to 5 minutes, with the mandrel fingers in a downward position. When the mandrel is removed from the solution, a web of solution forms almost immediately between the fingers of the mandrel. Usually, draining of solution from the coated mandrel is continued until the web disappears and all dripping has substantially stopped. The coated mandrel is placed, with the fingers pointing upward, in a convection oven or infrared dryer maintained at about 150° C. for a period of about 10 to 20 minutes to remove residual solvent. Lower temperatures can be used but longer drying times are needed. Higher temperatures and/or reduced pressures can shorten the drying time. After drying, the coated mandrel is allowed to cool to room temperature. Then, the glove is removed from the mandrel. The resultant glove produced by this procedure usually has a thickness of about 0.002 to 0.003 inch (0.05 to 0.075 mm). Such thin-walled gloves are particularly desired for surgical gloves.

Gloves may be double-dipped for increased thickness, as illustrated in Examples below. Draining, drying, and glove removal, etc., may be done in the usual manner. When using a double dip for increased glove thickness, the mandrel preferably is heated to about 85° C. prior to the first dip. Such preheating helps avoid non-uniformities, such as thick-thin spots, streaks, blisters, etc., in the resultant final article. Special gloves with fingers or fingers-and-palm area of extra thickness, e.g., 0.005-inch (0.127-mm) thickness, can be made with the double-dip procedure by dipping the mandrel to the appropriate depth during the first or second dip. Similar double-dipping procedures can be used to prepare gloves or other articles having multiple layers, each of the same or a different polymer.

Preferably, the mandrel has a matte surface, is shaped for optimum glove fit, and is made of aluminum or ceramic, the latter being most preferred. Usually, it is desirable to coat the mandrels with perfluoropolymers to facilitate removal of the completed article from the mandrel without damaging the article. Perfluoropolymer sprays, such as "RemGrit TLF 50", sold by Rem Chem Division of RemGrit Corporation, of Bridgeport, Connecticut, are suitable. Other release agents, such as silicone oil (e.g., Dow Corning FF-400) are also satisfactory for application to the mandrels before they are dipped in the polyurethaneurea solution. Alternatively, the release agents can be mixed with the polymer solution. Removal of the article from the mandrel is also made easier by dipping the mandrel with the formed article still in place into an aqueous solution of surfactants and then removing the article from the mandrel.

A cuff can be formed on a dried glove by rolling the "sleeve" (i.e., upper wrist portion) onto itself. It is preferable to do this while the glove is still hot (about 85° C.) so that the cuff material sticks to itself without additional heat. A well-defined demarcation line at the mandrel "elbow" aids the formation of cuffs. Note that following removal of the dipped mandrel with the fingers in the down position, sufficient "drip time" should be allowed to assure that enough solution and solvent drips from the mandrel, so that when the mandrel is inverted (fingers up) for final evaporation and removal of solvent, polymer solution will not flow below the demarcation line.

Anti-tack agents, such as stearates, talc, corn starch, and the like can be applied to the inside and/or outside of the glove before packaging. Alternatively, perfluoroethylene polymers can be sprayed onto the inside and/or outside of the glove to eliminate tackiness. It is preferred to apply the perfluoroethylene polymer while the glove is still hot to improve adhesion of the perfluoroethylene particles to the surface of the glove.

Another method of preparing tack-free gloves is to dip the mandrel sequentially into different baths, each containing a different polymer solution. In a preferred version of this method, a polyesterurethaneurea layer can be formed as a middle layer between layers of polyetherurethaneurea and/or polyvinylpyrrolidone. For compatibility with the polyesterurethaneurea, DMAC is the preferred solvent for each polymer solution used to produce the layered glove.

The strength, freedom from pin-holes and general integrity of the shaped article, especially when the article is a glove, condom, or the like, is of great importance to the performance of the article. Testing for strength and freedom from leaks due to pin holes is an important quality control measure. For example, measures of these two characteristics can be made while the article is still on the mandrel or forming mold. For example, the wrist portion of a glove fan be sealed to the mandrel with an inflatable collar and then a fixed volume of air or water can be injected into the glove. A measure of the strength of the glove is indicated by the initial pressure contained by the glove; the absence of pinholes is indicated by the maintenance of a constant pressure during a predetermined time interval. After testing, the glove is deflated and removed from the mandrel. In this way, each article may be subjected to leak testing before removal from the mandrel.

TEST PROCEDURES

Various characteristics and properties mentioned in the preceding discussion and reported in the examples below are determined by the following methods.

Solution viscosity is determined in accordance with the general method of ASTM D1343-69 with a Model DV-8 Falling Ball Viscometer, (sold by Duratech Corp., Waynesboro, Va.), operated at 30° C.

Glycol number average molecular weight is determined from the hydroxyl number of the polyether diol or polyester diol. Hydroxyl number is measured by the imidazole-pyridine catalyst method described in S. L. Wellon et al., "Determination of Hydroxyl Content of Polyurethane Polyols and Other Alcohols", Analytical Chemistry, vol. 51, No. 8, pp. 1374–1376 (July 1980).

The isocyanate end-group concentration in the capped prepolymer, NCO, is measured by the method of S. Siggia, "Quantitative Organic Analysis via Functional Group", 3rd Edition, Wiley & Sons, New York, pages 559–561 (1963).

Resistance to deformation and elastic properties of samples are measured in accordance with the general method of ASTM D273 1-72, except that the thread of the ASTM method is replaced by a sample of cast film of ⅛-inch (0.32-cm) width, 2-inch (5-cm) length and a measured thickness. Denier of the film is determined from the weight of a known length of a 0.32-cm-wide strip of the film. The samples are subjected to five 0 to 300% extension/retraction cycles at a constant elongation rate of 800% per minute. Load power is determined in milligrams per original denier and reported in the Examples below in deciNewtons per Tex for $LP_{100}$ and $LP_{200}$, by measuring the load on the sample during the first cycle as the sample is extended by 100% and 200%, respectively. After completion of the fifth cycle the film strip is relaxed for 30 seconds and its increase in length is determined as a percent of its unstretched original length and reported as percent set.

Tear strength of the film samples is determined in pounds force per inch of sample thickness by the general procedure of ASTM D470-82 and is reported in the Examples in Newtons per centimeter.

Puncture resistance is measured in accordance with a procedure in which a sample of film is held in a 3-½-inch-diameter (8.9-cm) circular holder in a flat, horizontal position and is then is penetrated by a vertical probe fitted with an sharp blade (i.e., a No. 10 Exacto knife blade) attached to the crosshead of an Instron testing machine, with the crosshead moving at a vertical rate of two inches per minute (5.1 cm/min). Puncture resistance is determined in pounds force per inch of sample thickness and is reported in the Examples in Newtons per cm.

The practical significance of the above described measurements with regard to typical articles of the invention (e.g., surgical gloves) is as follows. Load power at extensions of 100% and 200% represent the retractive force in a film or glove as it is stretched. An extension of 200% approximates the maximum stretch experienced when a glove is pulled on or removed. Because a glove must return to its original shape after being pulled on, a low value of no greater than 15% set is desired. High resistance to tear is needed for an article, such as a glove, to survive repeated pulling on and taking off. Puncture resistance is also highly desirable.

EXAMPLES

The invention is further illustrated by the following examples of preferred embodiments. These examples are included for purposes of illustration and are not intended to limit the scope of the invention, which scope is defined by the appended claims. The reported results are believed to be representative but do not constitute all the runs involving the indicated materials. In the Examples, samples of the invention are designated by Arabic numerals and comparison samples by uppercase letters.

In the Examples, known methods were used to prepare solutions of polyurethaneurea polymers. The procedure for preparing copolyurethaneurea from 2G/4G-6 of 3,400 molecular weight was in accordance with Martin, U.S. Pat. No. 4,340,527, Example II, column 5, line 61, through column 6, line 4. The procedure for preparing copolyetherurethaneureas based on THF/3MeTHF was according to the general procedure of Dreibelbis et al, U.S. Pat. No. 5,000,899, Example I, column 5, line 63 through column 6, line 12, and Ernst, U.S. Pat. No. 4,590,312, column 3, lines 13–27.

The particular ingredients employed in each procedure are listed in the examples. In all samples of the invention, diethylamine amounting to 5 mole % of total diamines was used as a chain terminator.

EXAMPLE 1

This example shows the superior physical properties of thin-walled articles of polyurethaneurea (Samples 1, 2 and 3) in accordance with the invention, as compared to thin-walled articles of polyurethanes or of latex (comparison Samples B, C and A, respectively). The example also illustrates the preparation of gloves in accordance with the process of the invention.

Samples 1, 2 and 3 were prepared in accordance with the procedures of the patents referred to above. Sufficient DMAC was added to adjust the solutions to about 20% solids and to a solution viscosity of about 125 poise. For the determination of physical properties, films were cast from the solution on polyester film with a doctor knife and then cut to size required for measurement of properties. Comparison Sample A specimens were cut from four pairs of commercial latex gloves of about 0.007 to 0.008 inch (0.18 to 0.20 ram) thickness. Samples 1–3 and comparison Samples B and C were each about 0.002 to 0.003 inch (0.051 to 0.076 mm) thick. The results are summarized in Table 1, below.

The data of Table 1 show that polyurethaneurea Samples 1, 2 and 3 of the invention (made with an EDA or HMPD chain extender) have considerably higher tear strength than latex comparison Sample A and polyurethane comparison Samples B and C (made with a 4G dihydroxy chain extender). Note that comparison polyurethane Sample B, which was made with capped prepolymer having a 1.5% NCO end group content, did not form a self-supporting films. When the NCO end group content of the polyurethane sample was raised to 1.8%, as for comparison Sample C, the comparison sample still had undesirably low tear strength and unacceptably high set. In contrast to the comparison samples, samples of the invention, i.e., Samples 1, 2 and 3, had desirably low set even when the capped prepolymer had a 1.5% NCO content. Samples 1 and 2 of the invention made from 2G/4G-6 copolyesterdiol had higher tear resistance and higher set than Sample 3 of the invention made from THF/3MeTHF copolyetherdiol, but the THF/3MeTHF polyurethaneurea had somewhat lower set. However, as indicated by the load power, all polyurethaneurea samples of the invention were stronger, but not excessively so, than the polyurethane samples and the latex samples.

TABLE 1

| Sample | Polyurethanes | | | Polyurethaneureas | | |
|---|---|---|---|---|---|---|
| | A | B | C | 1 | 2 | 3 |
| Glycol | (1) | 2G/4G-6 | 2G/4G-6 | 2G/4G-6 | 2G/4G-6 | THF/3MeTHF |
| Diisocyanate | (1) | MDI | MDI | MDI | PICM | MDI |
| % NCO | (1) | 1.50 | 1.00 | 1.50 | 1.50 | 1.80 |
| Extender | (1) | 4G | 4G | EDA | HMPD | EDA |
| Load Power at 100% | | | | | | |
| mg/den | 9 | (2) | 8 | 22 | 29 | 29 |
| (dN/tex) | 0.008 | (2) | 0.007 | 0.019 | .025 | 0.025 |
| at 200%, mg/den | 14 | (2) | 10 | 31 | (3) | 43 |
| (dN/tex) | 0.012 | (2) | 0.009 | 0.027 | (3) | 0.038 |
| % Set | 5 | (2) | 53 | 13 | 24 | 10 |
| Tear, lb/in | 57 | (2) | 20 | 109 | 140 | 79 |
| (N/cm) | 98 | (2) | 35 | 191 | 245 | 138 |

Notes
(1) not applicable
(2) sample too tacky and not self-supporting
(3) no measurement made The following procedure was used to fabricate gloves of about 0.0025-inch (0.064-mm) thickness from polymer solutions of the invention. A solution having a polymer solids content of 15% in DMAC solvent and viscosity of 80 poise was prepared. Cyanox* 1790 phenolic antioxidant (sold by American Cyanamid Co.) was added to the solution to provide a 1.5% concentration of the antioxidant, based on the weight of the polymer. A polar organopolysiloxane, Dow Corning FF-400*, amounting to 1 weight percent based on polymer, was also added to the solution to facilitate the removal of finished gloves from the mandrels. This solution was degassed at room temperature by applying a vacuum of 2 mm Hg for 5 minutes.

A ceramic mandrel of desired size and shape, and coated with polytetrafluorethylene (PTFE) release agent was dipped into the solution at an angle of 85 degrees to the horizontal with the mandrel in a fingers-down, palm-up position. The mandrel was dipped at a vertical speed of 300 cm per minute and held in the solution for 10 seconds. The mandrel, with a continuous coating of polymer adhering to its surface, was then removed at the same speed in the same configuration and allowed to drain for 2 minutes. Transient webs between the fingers separated after 1 to 2 minutes, during which time dripping from finger tips also stopped. The mandrel was then inverted into a fingers-up, palm-up position and placed in a dryer maintained at 150° C. for 10 minutes. During the drying, an initial "wet sheen" appearance of the glove turned to a more subdued sheen. After removal from the oven and cooling to 100° C., a cuff was formed on the dried glove by rolling the glove sleeve (i.e., the portion above the wrist) two turns on itself. The mandrel was then cooled to room temperature; the glove was powdered with talcum, and then removed from the mandrel.

All of the thin-walled gloves of the invention had good tactility, elasticity, tear, and puncture resistance. Gloves made from solutions of Sample 1 were deemed to have the best overall characteristics and superior in puncture resistance and strength to commercial latex gloves of more than twice the thickness. (Typical puncture resistance measurements are shown in Example 5 below.)

A double dipping process was used to prepare gloves of the same compositions as above with thicker walls to provide the gloves with even greater resistance to tearing and puncture while still maintaining satisfactory tactility. A mandrel, as described above, was heated to 90° C. and then immersed for 10 seconds in degassed polymer solution maintained at room temperature. The mandrel was tilted at an 85-degree angle in fingers-down, palm-up position when dipped and withdrawn, both at a speed of 250 cm/min. Excess solution was drained with the mandrel in the same position for 2 minutes. The mandrel was then inverted and dried in a convection oven at 150° C. for 10 minutes. The coated mandrel was removed from the oven, cooled to room temperature and dipped a second time in the solution, using the same sequence of steps as for the first dip. For some samples, the second dip was used to coat fingers only, fingers and palm, or the entire hand. Satisfactory gloves of the invention were produced.

EXAMPLE 2

This example illustrates the effects of the ratio 2G/4G and molecular weight in the glycol of copolyester-based polyurethaneureas. Solutions of polymers were prepared according to the general procedure of Example 1, with minor adjustments being made to produce the polymers described in Table 2 below. All polymers of this example were produced with 2G/4G-6 glycol, MDI diisocyanate, 1.50% NCO end group content of the capped prepolymer, HMPD chain extender and 5 mole % (based on total diamines) of diethylamine chain terminator were employed. Films were cast from the polymer solutions and their properties determined as in Example 1.

TABLE 2

|  | Sample | | | | | | |
|---|---|---|---|---|---|---|---|
|  | 4 | 5 | 6 | 7 | 8 | 9 | 10 |
| Glycol MW | 3710 | 6056 | 3000 | 3400 | 5141 | 3182 | 6124 |
| 2G/4G ratio | 20/80 | 28/72 | 46/54 | 60/40 | 60/40 | 75/25 | 80/20 |
| $LP_{100}$, mg/den | 15 | 15 | 15 | 15 | 15 | 13 | 12 |
| (dN/Tex) | 0.013 | 0.013 | 0.013 | 0.013 | 0.013 | 0.011 | 0.010 |
| % Set | 31 | 30 | 14 | 13 | 12 | 15 | 24 |
| Tear, lb/in | 139 | 128 | 111 | 89 | 85 | 77 | 71 |
| (N/cm) | 243 | 224 | 194 | 156 | 149 | 135 | 124 |

The data indicate that 2G/4G ratios in the range of 20:80 to 80/20 can be useful, but ranges of 35:65 to 75:25 are much preferred, because of lower set. Glycol molecular weights in excess of 2500 are useful, but preferably are in the range is 3000 to 6000. The ratio of 2G/4G apparently has stronger effects than the glycol molecular weight within the ranges of this example.

EXAMPLE 3

The effects of different chain-extension agents on polyurethaneurea polymers made with 2G/4G-6 glycol in accordance with the invention are illustrated in this example. Polymer solutions were prepared according to the procedure of Example 1, with adjustments being made to produce the polymers described in Table 3 below. The table also summarizes the properties of films cast from the solutions. For each sample, MDI, 1.50% NCO, and 2G/4G-6 (60/40) of 3400 number average molecular weight were used to prepare the polymers. For comparison, data on films of Samples 7 (Example 2) and 1 (Example 1) are included in Table 3.

TABLE 3

|  | Sample | | | | |
|---|---|---|---|---|---|
|  | 7 | 1 | 11 | 12 | 13 |
| Extender | HMPD | EDA | MXD | 1,3-PDA | 1,2-PDA |
| $LP_{100}$, mg/den | 15 | 22 | 20 | 17 | 18 |
| (dN/Tex) | 0.013 | 0.019 | 0.018 | 0.015 | 0.016 |
| % Set | 13 | 13 | 22 | 23 | 21 |
| Tear, lb/in | 89 | 109 | 85 | 87 | 97 |
| (N/cm) | 156 | 191 | 149 | 152 | 170 |

The data indicate the suitability of HMPD, EDA, MXD, 1,3-PDA, AND 1,2-PDA as chain extenders for the polymers intended for making thin-walled articles in accordance with the invention. As shown in Table 3, the best balance of elastic properties (i.e., low, but sufficient, load power and low % set) accompanied by high tear strength and puncture resistance is provided when HMPD or EDA was employed as chain extenders. Accordingly, HMPD and EDA are preferred for use in polyurethaneureas made with 2G/4Go6 and MDI. HMPD is preferred over EDA because of more favorable tactile properties.

EXAMPLE 4

This example compares the properties of films cast from solutions of two different polyurethaneurea polymers, made by the general procedures of the preceding examples with MDI, 1.80% NCO and THF/3MeTHF (85/15) of 3855 number average molecular weight. One polymer was made with HMPD chain-extender (Sample 14); the other, with EDA (Sample 3 of Example 1) chain-extender. Physical properties of the films are summarized in Table 4 below and support the preference for EDA over HMPD in polyurethaneureas formed with TFH/3MeTHF copolyether glycol and MDI.

TABLE 4

|  | Sample | |
|---|---|---|
|  | 14 | 3 |
| Extender | HMPD | EDA |
| $LP_{100}$, mg/den | 22 | 29 |
| (dN/Tex) | 19 | 26 |
| $LP_{200}$, mg/den | 31 | 43 |
| (dN/Tex) | 27 | 38 |
| % Set | 10 | 10 |
| Tear, lb/in | 52 | 79 |
| (N/cm) | 91 | 138 |

EXAMPLE 5

This example compares the puncture resistance of thin-walled films made with typical polymer compositions in accordance with the invention with that of strips cut from commercial surgical gloves of rubber latex. The film samples of the invention were about 0.0025-inch (0.064-ram) thick and the rubber latex samples were about 0.0075-inch (0.191-ram) thick. The samples of the invention were prepared in accordance with the procedures of Example 1. Table 5 summarizes their puncture properties. Samples 14 and 15 of the invention each were made with 85/15 THF/3MeTHF prepolymer of 3400 number average molecular weight. Samples 16 and 17 of the invention were made with 60/40 2G/4G-6 prepolymer of 3400 number average molecular weight. MDI was the diisocyanate used for each sample of the invention. The chain extender and % NCO employed are listed in Table 5 below, along with the measured puncture resistance of the film sample. Note that for increased puncture resistance in thin-walled articles in accordance with the invention, HMPD is a preferred chain extender for polyetherurethaneureas and EDA is a preferred for polyesterurethaneureas. Note also, the great superiority in puncture resistance possessed by Samples 14–17 in accordance with the invention over the Sample D taken from conventional rubber latex surgical gloves.

TABLE 5

| Sample | % NCO | Extender | Puncture Resistance lb/in | N/cm |
|---|---|---|---|---|
| Copolyetherurethaneurea | | | | |
| 14 | 1.8 | EDA | 62 | 109 |
| 15 | 1.5 | HMPD | 79 | 138 |
| Copolyesterurethaneurea | | | | |
| 16 | 1.8 | EDA | 100 | 175 |
| 17 | 1.5 | HMPD | 80 | 140 |
| Rubber Latex | | | | |
| D | — | — | 25 | 44 |

We claim:

1. A process for fabricating a thin-walled elastic article comprising preparing a polyetherurethaneurea by reacting methylene-bis(4-phenylisocyanate) with a polyether diol derived from a homopolymer of tetrahydrofuran or a copolymer of tetrahydrofuran and 3-methyltetrahydrofuran in a weight ratio in the range of 96/4 to 80/20, said polyether diol having a number average molecular weight in the range of 3,000 to 6,000, to form an isocyanate-capped prepolymer having an isocyanate group content in the range of 1.4 to 2.0 weight %, and then chain-extending the isocyanate-capped prepolymer with ethylenediamine or 1,3-diaminocyclohexane to form the polyetherurethaneurea, forming a solution of the polyetherurethaneurea in an organic solvent that is substantially free of metal chlorides, the polyetherurethaneurea being present in the solution at a concentration in the range of 12% to 20% by total solution weight, and the solution having a viscosity, measured at 30° C., in the range of 25 to 125 poise, degassing the thusly formed polyetherurethaneurea solution, dipping a mandrel into the solution and then removing the mandrel therefrom to form a solution-coated mandrel, drying the coated mandrel and removing the resulting dried thin-walled article from the mandrel.

2. A process in accordance with claim 1 wherein the diamine chain extender is ethylene diamine.

* * * * *